United States Patent
Sittenauer et al.

(10) Patent No.: US 12,029,818 B2
(45) Date of Patent: Jul. 9, 2024

(54) LAPATINIB PARTICLES AND USES THEREOF

(71) Applicant: CRITITECH, INC., Lawrence, KS (US)

(72) Inventors: Jacob Sittenauer, Lawrence, KS (US); Joseph Farthing, Lawrence, KS (US); Mark Williams, Lawrence, KS (US); Michael Baltezor, Lawrence, KS (US); Gere Dizerega, Lawrence, KS (US); Aranza Barreda Abarca, Lawrence, KS (US); Shelby Clark, Lawrence, KS (US)

(73) Assignee: CRITITECH, INC., Lawrence, KS (US)

( * ) Notice: Subject to any disclaimer, the term of this patent is extended or adjusted under 35 U.S.C. 154(b) by 0 days.

(21) Appl. No.: 17/812,479

(22) Filed: Jul. 14, 2022

(65) Prior Publication Data

US 2022/0370355 A1    Nov. 24, 2022

Related U.S. Application Data

(63) Continuation of application No. 17/381,786, filed on Jul. 21, 2021, now abandoned.

(60) Provisional application No. 63/055,788, filed on Jul. 23, 2020.

(51) Int. Cl.
*A61K 9/14* (2006.01)
*A61K 31/5365* (2006.01)
*A61K 47/26* (2006.01)

(52) U.S. Cl.
CPC ............ *A61K 9/14* (2013.01); *A61K 31/5365* (2013.01); *A61K 47/26* (2013.01)

(58) Field of Classification Search
CPC ...... A61K 9/14; A61K 31/5365; A61K 47/26; A61K 9/0019; A61K 9/10; A61K 9/1688; A61K 31/4196; A61K 31/7068; A61K 47/32; A61K 47/38; A61K 31/517; A61P 31/00; A61P 35/00
See application file for complete search history.

(56) References Cited

U.S. PATENT DOCUMENTS

| 8,586,091 B2 | 11/2013 | Rimkus |
| 9,827,230 B2 | 11/2017 | Brisander et al. |

FOREIGN PATENT DOCUMENTS

| WO | 2015145145 A1 | 10/2015 |
| WO | 2016/197091 | 12/2016 |
| WO | 2019/067851 | 4/2019 |
| WO | 2019/067866 | 4/2019 |

OTHER PUBLICATIONS

Baltezor et al. Aggregated High Surface Area Particle Technology for Pulmonary Drug Delivery, Respiratory Drug Delivery 2020.
Diaz et al. Antitumor and antiangiogenic effect of the dual EGFR and HER-2 tyrosine kinase inhibitor lapatinib in a lung cancer model, BMC Cancer 2010, 10:188.
Tykerb PI Revised Dec. 2018.
International Search Report and Written Opinion for PCT/US2021/042554 mailed Nov. 10, 2021.

*Primary Examiner* — Jessica Worsham
(74) *Attorney, Agent, or Firm* — MCDONNELL BOEHNEN HULBERT & BERGHOFF LLP (57) ABSTRACT

The disclosure provides particles of at least 95% by weight of lapatinib, or a pharmaceutically acceptable salt thereof, wherein the particles have a specific surface area (SSA) of at least 10 $m^2/g$ and have a mean particle size by volume distribution of between about 0.7 μm and about 8 μm.

17 Claims, 5 Drawing Sheets

Figure 3. Powder X-ray Diffraction Patterns

LAPATINIB PARTICLES AND USES THEREOF

CROSS REFERENCE

This application is a continuation of U.S. patent application Ser. No. 17/381,786, filed Jul. 21, 2021, which claims priority to U.S. Provisional Application No. 63/055,788, filed Jul. 23, 2020, both of which are incorporated by reference herein in their entirety.

BACKGROUND

Dissolution rate is a key parameter in determining the rate and extent of drug absorption and bioavailability. Poor aqueous solubility and poor in vivo dissolution are limiting factors for in vivo bioavailability of many drugs. Thus, in vitro dissolution rates are recognized as an important element in drug development, and methods and compositions for increasing the dissolution rates of poorly soluble drugs are needed.

SUMMARY

In one aspect, the disclosure provides compositions, comprising particles comprising at least 95% by weight of lapatinib, or a pharmaceutically acceptable salt thereof, wherein the particles have a specific surface area (SSA) of at least 10 $m^2/g$ and have a mean particle size by volume distribution of between about 0.7 µm and about 8 µm. In various embodiments, the particles have a SSA of at least 15 $m^2/g$ or at least 18 $m^2/g$,. In other embodiments, the particles have a SSA of between 10 $m^2/g$ and 50 $m^2/g$, between 15 $m^2/g$ and 50 $m^2/g$, or between 18 $m^2/g$ and 50 $m^2/g$. In another embodiment, the particles have a mean particle size by volume distribution of between about 0.7 µm and about 8 µm. In one embodiment, the particles comprise at least 96%, 97%, 98%, 99%, or 100% of lapatinib, or a pharmaceutically acceptable salt thereof. In another embodiment, wherein the particles are uncoated and exclude polymer, protein, polyethoxylated castor oil and polyethylene glycol glycerides composed of mono-, di- and triglycerides and mono- and diesters of polyethylene glycol. In one embodiment, the composition comprises a suspension further comprising a pharmaceutically acceptable liquid carrier. In another embodiment, the composition further comprises one or more components selected from the group consisting of polysorbate, methylcellulose, polyvinylpyrrolidone, mannitol, and hydroxypropyl methylcellulose. In a further embodiment,
  (a) the particles have a mean bulk density between about 0.005 $g/cm^3$ and about 0.100 $g/cm^3$, between about 0.010 $g/cm^3$ and about 0.075 $g/cm^3$, between about 0.010 $g/cm^3$ and about 0.050 $g/cm^3$, or between about between about 0.015 $g/cm^3$ and about 0.040 $g/cm^3$, tapped or not tapped; and/or
  (b) the particles have a mean bulk density less than about 0.100 $g/cm^3$, 0.090 $g/cm^3$, 0.080 $g/cm^3$, 0.070 $g/cm^3$, 0.060 $g/cm^3$, 0.040 $g/cm^3$, or 0.030 $g/cm^3$, tapped or not tapped.

In one embodiment, the pharmaceutically acceptable salt of lapatinib comprises lapatinib ditosylate monohydrate.

In another aspect, the disclosure provides methods for treating a tumor, comprising administering to a subject with a tumor an amount effective to treat the tumor of the composition of embodiment of the disclosure. In various embodiments, the tumor is a breast tumor, pancreatic carcinoma, prostate carcinoma, bladder carcinoma, lung carcinoma, ovarian carcinoma, gastrointestinal tumor, or renal cell tumor. In other embodiments, the tumor is a breast tumor, and wherein the breast tumor is an advanced or metastatic breast tumor that overexpresses human epidermal growth factor 2 (HER2), or a hormone receptor positive metastatic breast tumor that overexpresses the HER2 receptor. In a further embodiment, the method further comprises administering capecitabine and/or letrozole to the subject. In other embodiments, the subject is a human subject, including but not limited to a female human subject, including but not limited to a post-menopausal female human subject. In one embodiment, the composition is administered by intra-tumoral injection, peri-tumoral injection, intra-peritoneal injection, or is administered into a mammary fat pad.

In another aspect, the disclosure provides methods for making lapatinib particles, comprising:
  (a) introducing (i) a solution comprising at least one solvent selected from the group consisting of acetone and DCM, or combinations thereof, and at least one solute comprising lapatinib or a pharmaceutically acceptable salt thereof into a nozzle inlet, and (ii) a compressed fluid into an inlet of a vessel defining a pressurizable chamber;
  (b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 µm and 125 µm;
  (c) contacting the atomized droplets with the compressed fluid, to cause depletion of the solvent from the atomized droplets, to produce compound particles comprising at least 95% lapatinib or a pharmaceutically acceptable salt thereof, wherein the particles have a specific surface area (SSA) of at least 10 $m^2/g$ and have a mean particle size by volume distribution of between about 0.7 µm and about 8 µm,
  wherein steps (a), (b), and (c) are carried out under supercritical temperature and pressure for the compressed fluid.

In one embodiment, the method further comprises
  (d) contacting the compound particles produced in step (c) with an anti-solvent to cause further depletion of the solvent from the compound particles, wherein step (d) is carried out under supercritical temperature and pressure for the anti-solvent.

In one embodiment, a flow rate of the solution through the nozzle has a range from about 0.5 mL/min to about 30 mL/min. In another embodiment, the sonic energy source comprises one of a sonic horn, a sonic probe, or a sonic plate. In a further embodiment, the sonic energy source has a frequency between about 18 kHz and about 22 kHz, or about 20 kHz. In one embodiment, the method further comprises
  (e) receiving the plurality of particles through the outlet of the pressurizable chamber; and
  (f) collecting the plurality of particles in a collection device.

In another embodiment, the compressed fluid is super critical carbon dioxide. In a further embodiment, the anti-solvent is super critical carbon dioxide. In various embodiments, the solvent may include, but is not limited to acetone, ethanol, methanol, or combinations thereof. In one embodiment, the solvent comprises acetone. In another embodiment, the method is carried. out between 31.1° C. to about 60° C., and at between about 1071 psi and about 1800 psi. In a further embodiment, the particles have a SSA of at least 15 m²/g or at least 18 m²/g. In another embodiment, the disclosure provides compound particles prepared by the method of any embodiment of the disclosure.

DESCRIPTION OF THE FIGURES

FIG. 1(A-D). Scanning Electron Microscopy Micrographs (A) Raw material lapatinib 2500X, (B) Raw material lapatinib 5000X, (C) Lapatinib processed using acetone as solvent 10,000X, (D) Lapatinib processed using acetone as solvent 20,000X.

FIG. 2(A-B) Scanning Electron Microscopy Micrographs (A) Lapatinib processed using DCM. as solvent 2500X, (B) Lapatinib processed using DCM. as solvent 20,000X, FIG. 3. Powder X-ray Diffraction Patterns from acetone and DCM compared to the lapatinib raw material FIG. 4. Powder X-ray Diffraction Patterns from a 14 day, room temperature stability study showing conversion of the amorphous form of SCP lapatinib to a crystalline form FIG. 5. Dissolution of Lapatinib in pH=7, 50% EtOH-Water at 50 rpm and 37° C. showing large difference in dissolution due to the increased surface area of the SCP Lapatinib

DETAILED DESCRIPTION

All references cited are herein incorporated by reference in their entirety. As used herein, the singular forms "a", "an" and "the" include plural referents unless the context clearly dictates otherwise. All embodiments of any aspect of the disclosure can be used in combination, unless the context clearly dictates otherwise.

As used herein. "about" means +/−5% of the recited value.

In one aspect, the disclosure provides compositions, comprising particles comprising at least 95% by weight of lapatinib, or a pharmaceutically acceptable salt thereof, wherein the particles have a specific surface area (SSA) of at least 10 m²/g and have a mean particle size by volume distribution of between about 0.7 μm and about 8 μm.

As used herein, "lapatinib" includes any ionization state of lapatinib, including base, acid, and neutral states.

The "lapatinib particles" refers to particles of lapatinib that do not include an added excipient. Lapatinib particles are different than "particles containing lapatinib", which are particles that contain lapatinib and at least one added excipient. Lapatinib particles of the disclosure exclude a polymeric, wax or protein excipient and are not embedded, contained, enclosed or encapsulated within a. solid excipient. Lapatinib particles of the disclosure may, however, contain impurities and byproducts typically found during preparation of lapatinib. Even so, lapatinib particles comprise at least 95%, at least 96%. at least 97%, at least 98%, at least 99% or 100% lapatinib, or a pharmaceutically acceptable salt thereof, meaning the lapatinib particles consist of or consist essentially of substantially pure lapatinib or pharmaceutically acceptable salt of lapatinib.

As used herein, the "specific surface area" is the total surface area of the lapatinib particle per unit of lapatinib mass as measured by the Brunauer-Emmett-Teller ("BET") isotherm (i.e.: the BET SSA). As will be understood by those of skill in the art, the SSA is determined on a per gram basis and takes into account both agglomerated and non-agglomerated lapatinib particles in the composition. The BET specific surface area test procedure is a compendial method included in both the United States Pharmaceopia and the European Pharmaceopeia. The lapatinib particles have a specific surface area (SSA) of at least 10 m²/g. In various further embodiments, the lapatinib particles have a SSA of at least 11 m²/g, 12 m²/g, 13 m²/g, 14 m²/g, 15 m²/g, 16 m²/g, 17 m²/g, 18 m²/g, or 19 m²/g. In a further embodiment, the lapatinib particles have a SSA of between 10 m²/g and about 50 m²/g, about 12 m²/g and about 50 m²/g, about 15 m²/g and about 50 m²_/g, between about 17.5 m²/g and about 50 m²/g, between about 18 m²/g and about 50 m²/g, between about 20 m²/g and about 50 m²/g, between about 17.5 m²/g and about 45 m²/g, between about 17.5 m²/g and about 40 m²/g, between about 17.5 m²²/g and about 35 m²g, between about 17.5 m²/g and about 30 m²/g, or between about 17.5 m²/g and about 25 m²/g, between about 19 m²/g and about 50 m²/g, between about 19 m²/g and about 45 m²/g, between about 19 m²/g and about 40 m²/g, between about 19 m²/g and about 35 m²/g, between about 19 m²/g and about 30 m²/g, or between about 19 m²/g and about 25 m²/g.

In various embodiments, the particles have a mean bulk density between about 0.005 g/cm³ and about 0.100 g/m³, Structure of lapatinib Lapatinib chemical name:

N-(3-chloro-4-{[(3-fluorophenyl)methyl]oxy}phenyl)-6-[5-({[2-(methylsulfonyl)ethyl]amino}methyl)-2-furanyl]-4-quinazolinamine.

between about 0.010 g/cm³ and about 0.075 g/cm³, between about 0.010 g/cm³ and about 0.050 g/cm³, or between about between about 0.015 g/cm³ and about 0.040 g/cm³, tapped or not tapped. In various other embodiments, the particles have a mean bulk density less than about 0.100 g/cm³, 0.090 g/cm$^3$, 0.080 g/cm$^3$, 0,070 g/cm$^3$, 0.060 g/cm$^3$, 0.050 g/cm$^3$, 0.040 g/cm$^3$, or 0.030 g/cm$^3$, tapped or not tapped.

As used herein, the bulk density (not tapped) of a particle is the ratio of the mass to the volume (including the interparticulate void volume) of an untapped powder sample.

As used herein, the tapped density of a particle is obtained by mechanically tapping a graduated cylinder containing the sample until little further volume change is observed.

The lapatinib particles have a mean particle size by volume distribution of from about 0.7 micron to about 8 microns in diameter. In some embodiments, the lapatinib particles have a mean particle size by volume distribution of from about 1 micron to about 8 microns in diameter, or about 1.5 microns to about 7 microns in diameter. The lapatinib particles are in a size range where they are unlikely to be carried out of the tumor by systemic circulation and yet benefit from the high specific surface area to provide enhanced solubilization and release of the drug.

In any of these various embodiments, the lapatinib particles may include, for example, at least $5 \times 10^{-15}$ gram lapatinib or a pharmaceutically acceptable salt thereof per lapatinib particle, or between about $1 \times 10^{-8}$ and about $5 \times 10^{-15}$ gram lapatinib, or a pharmaceutically acceptable salt thereof per lapatinib particle.

In one embodiment, the particles are uncoated and exclude polymer, protein, polyethoxylated castor oil and polyethylene glycol glycerides composed of mono-, di- and triglycerides and mono- and diesters of polyethylene glycol.

In a further embodiment, the composition comprises a suspension further comprising a pharmaceutically acceptable liquid carrier. The suspension of the disclosure comprises lapatinib particles and a liquid carrier. The liquid carrier can be aqueous or non-aqueous. Even though the lapatinib particles do not include an added excipient, the liquid carrier of the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise lapatinib particles, water, buffer and salt. It optionally further comprises a surfactant. In some embodiments, the suspension consists essentially of or consists of water, lapatinib particles suspended in the water and buffer. The suspension can further contain an osmotic salt.

In one embodiment, the composition further comprises one or more components selected from the group consisting of polysorbate, methylcellulose, polyvinylpyrrolidone, mannitol, and hydroxypropyl methylcellulose.

The suspension can comprise one or more surfactants. Suitable surfactants include by way of example and without limitation polysorbates, lauryl sulfates, acetylated monoglycerides, diacetylated monoglycerides, and poloxamers.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

In one embodiment especially suitable for intraperitoneal (IP) administration, the suspension may be formulated to be hyperosmolar (hypertonic), hyposmolar (hypotonic) or isosmolar (isotonic) with respect to the fluid(s) of the IP cavity.

In some embodiments, the suspension may be isotonic with respect to fluid in the IP cavity. In such an embodiment, the osmolality of the suspension can range from about 200 to about 380, about 240 to about 340, about 280 to about 300 or about 290 mOsm/kg.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl)methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, polysorbate 80, and propylene glycol; polyvinyl alcohol from about 0.1 to about 4% povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid. fumaric acid and other alpha hydroxy acids, hydrochloric acid, ascorbic acid, and nitric acid and others known to those of ordinary skill in the art.

The suspension can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE®, octoxynol and others known to those of ordinary skill in the art.

The suspension can comprise one or more viscosity modifiers that increase or decrease the viscosity of the suspension. Suitable viscosity modifiers include methylcellulose, hydroxypropyl methylcellulose, mannitol and polyvinylpyrrolidone.

The suspension can comprise one or more osmotic agents such as those used for peritoneal dialysis. Suitable osmotic agents include icodextrin (a glucose polymer), sodium chloride, potassium chloride, and salts that are also used as buffering agents.

As used herein, "pharmaceutically acceptable salts" of lapatinib are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the lapatinib. The term "salts" refers to the relatively non-toxic, inorganic and organic acid addition salts of lapatinib. Representative salts include the hydrobromide, hydrochloride, sulfate, bisulfate, nitrate, acetate, oxalate, valerate, oleate, palmitate, stearate, laurate, malate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-1-19 which is incorporated herein by reference.) In one embodiment, the pharmaceutically acceptable salt of lapatinib comprises lapatinib malate.

In one embodiment, the composition comprises a dosage form of lapatinib in suspension (i.e.: with a pharmaceutically acceptable carrier and any other components), in a dosage deemed suitable by an attending physician for an intended use. Any suitable dosage form may be used; in various non-limiting embodiments, the dosage form is adequate to provide about 0.01 mg/kg to about 50 mg/kg of body weight per day. In various further embodiments, the dosage form is adequate to provide about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg of body weight per day. The suspension can be administered as is or can be diluted with a diluent, e.g. with saline water for injection optionally including a buffering agent and one or more other excipients, prior to administration. For example, the volume ratio of suspension to diluent might be in the range of 1:1-1:100 (v/v) or other suitable ratio.

In another aspect, the disclosure provides methods for treating a tumor, comprising administering to a subject with a tumor an amount effective to treat the tumor of the composition or suspension of any embodiment or combination of embodiments of the disclosure. The increased specific surface area of the lapatinib particles of the disclosure results in the significant increase in dissolution rate for the particles compared to currently available lapatinib. This provides a significant improvement for use of the particles of the disclosure in, for example, tumor treatment. Furthermore, in some embodiments the methods of the present disclosure can reduce the dosing frequency and side effects of lapatinib. By way of non-limiting example, a lapatinib dose administered by direct tumoral injection would be substantially less and the dosing frequency would be less compared to oral dosing, and side effects would also be expected to be lower since the systemic concentrations would be greatly reduced.

As used herein, a "tumor" includes benign tumors, pre-malignant tumors, malignant tumors that have not metastasized, and malignant tumors that have metastasized.

The methods of the disclosure can be used to treat tumor that is susceptible to lapatinib treatment, including but not limited to breast tumors, pancreatic carcinomas, prostate carcinomas, bladder carcinomas, lung carcinomas, ovarian carcinomas, gastrointestinal tumors, or renal cell tumors. In one embodiment, the tumor is a breast tumor, and the breast tumor is an advanced or metastatic breast tumor that overexpresses human epidermal growth factor 2 (HER2), or a hormone receptor positive metastatic breast tumor that overexpresses the HER2 receptor. In another embodiment, the method further comprises administering capecitabine and/or letrozole to the subject.

The subject may be any suitable subject with a tumor, including but not limited to humans, primates, dogs, cats, horses, cattle, etc. In one embodiment, the subject is a human subject, including but not limited to a female human subject, including but not limited to a post-menopausal female human subject.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Amounts effective for these uses depend on factors including, but not limited to, the nature of the lapatinib (specific activity, etc.), the route of administration, the stage and severity of the disorder, the weight and general state of health of the subject, and the judgment of the prescribing physician. It will be understood that the amount of the composition of suspension of the disclosure actually administered will be determined by a physician, in the light of the above relevant circumstances. In one non-limiting embodiment, an amount effective is an amount that provides between 0.01 mg/kg to about 50 mg/kg of body weight per day.

The compositions may be administered via any suitable route, including but not limited to orally, pulmonary, intraperitoneally, intra-tumorally, peri-tumorally, subcutaneous injection, intramuscular injection, administered into a mammary fat pad, or any other form of injection, as deemed most appropriate by attending medical personnel in light of all factors for a given subject A dosing period is that period of time during which a dose of lapatinib particles in the composition or suspension is administered. The dosing period can be a single period of time during which the entire dose is administered, or it can be divided into two or more periods of time during each of which a portion of the dose is administered.

A post-dosing period is that period of time beginning after completion of a prior dosing period and ending after initiating a subsequent dosing period. The duration of the post-dosing period may vary according to a subject's clinical response to the lapatinib. The suspension is not administered during the post-dosing period. A post-dosing period can last at least 7 days, at least 14 days, at least 21 days, at least 28 days, at least 35 days, at least 60 days or at least 90 days or longer. The post-dosing period can be kept constant for a subject or two or more different post-dosing periods can be used for a subject.

A dosing cycle includes a dosing period and a post-dosing period. Accordingly, the duration of a dosing cycle will be the sum of the dosing period and the post-dosing period. The dosing cycle can be kept constant for a subject or two or more different dosing cycles can be used for a subject.

In one embodiment, the administering is carried out more than once, and wherein each administration is separated in time by at least 21 days.

In another aspect, the disclosure provides methods for making compound particles, comprising:
- (a) introducing (i) a solution comprising at least one solvent selected from the group consisting of acetone and DCM, or combinations thereof, and at least one solute comprising lapatinib or a pharmaceutically acceptable salt thereof into a nozzle inlet, and (ii) a compressed fluid into an inlet of a vessel defining a pressurizable chamber;
- (b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 μm and 125 μm;
- (c) contacting the atomized droplets with the compressed fluid, to cause depletion of the solvent from the atomized droplets, to produce compound particles comprising at least 95% lapatinib or a pharmaceutically acceptable salt thereof, wherein the particles have a specific surface area (SSA) of at least 10 m$^2$/g and have a mean particle size by volume distribution of between about 0.7 μm and about 8 μm, wherein steps (a), (b), and (c) are carried out under supercritical temperature and pressure for the compressed fluid.

The methods utilize a sonic energy source located directly in the output stream of the solute dissolved in the solvent. Any suitable source of sonic energy may be used that is compatible with the methods of the disclosure, including but not limited to sonic horn, a sonic probe, or a sonic plate. In various embodiments, the nozzle orifice is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 nun, about 8mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm. about 16 mm and about 20 mm, about 16 mm and about 18 mm, and about 18 mm and about 20 mm, from the sonic energy source. In further embodiments, the nozzle assembly of any embodiment of WO2016/197091 may be used.

Any suitable source of sonic energy may be used that is compatible with the methods of the disclosure, including but not limited to sonic horn, a sonic probe, or a sonic plate. In various further embodiments, the sonic energy source produces sonic energy with an amplitude between about 10% and about 100% of the total power that can be generated using the sonic energy source. In light of the teachings herein, one of skill in the art can determine an appropriate sonic energy source having a specific total power output to be used, In one embodiment, the sonic energy source has a total power output of between about 500 and about 900 watts; in various further embodiments, between about 600 and about 800 watts, about 650-750 watts, or about 700 watts.

In various further embodiments, the sonic energy source produces sonic energy with a power output between about 20% and about 100%, about 30% and about 100%, about 40% and about 100%, about 50% and about 100%, about 60% and about 100%, about 70% and about 100%, about 80% and about 100%, about 90% and about 100%, about 10% and about 90%, about 20% and about 90%, about 30% and about 90%, about 40% and about 90%, about 50% and about 90%, about 60% and about 90%, about 70% and about 90%, about 80% and about 90%, about 10% and about 80%, about 20% and about 80%, about 30% and about 80%, about 40% and about 80%, about 50% and about 80%, about 60% and about 80%, about 70% and about 80%, about 10% and about 70%, about 20% and about 70%, about 30% and about 70%, about 40% and about 70%, about 50% and about 70%, about 60% and about 70%, about 10% and about 60%, about 20% and about 60%, about 30% and about 60%, about 40% and about 60%, about 50% and about 60%, about 10% and about 50%, about 20% and about 50%, about 30% and about 50%, about 40% and about 50%, about 10% and about 40%, about 20% and about 40%, about 30% and about 40%, about 10% and about 30%, about 20% and about 30%, about 10% and about 20%, or about 10%, 20%, 30%, 40%, 50%, 60%, 70%, 80%, 90%, or about 100% of the total power that can be generated using the sonic energy source. In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or a frequency of about 20 kHz on the sonic energy source is utilized.

In various further embodiments, the nozzle orifice has a diameter of between about 20 μm and about 125 μm, about 20 μm and about 115 μm, about 20 μm and about 100 μm, about 20 μm and about 90 μm, about 20 μm and about 80 μm, about 20 μm and about 70 μm, about 20 μm and about 60 μm, about 20 μm and about 50 μm, about 20 μm and about 40 μm, about 20 μm and about 30 μm, between about 30 μm and about 125 μm, about 30 μm and about 115 μm, about 30 μm and about 100 μm, about 30 μm and about 90 μm, about 30 μm and about 80 μm, about 30 μm and about 70 μm, about 30 μm and about 60 μm, about 30 μm and about 50 μm, about 30 μm and about 40 μm, between about 40 μm and about 125 μm, about 40 μm and about 115 μm, about 40 μm and about 100 μm, about 40 μm and about 90 μm, about 40 μm and about 80 μm, about 40 μm and about 70 μm, about 40 μm and about 60 μm, about 40 μm and about 50 μm, between about 50 μm and about 125 μm, about 50 μm and about 115 μm, about 50 μm and about 100 μm, about 50 μm and about 90 μm, about 50 μm and about 80 μm, about 50 μm and about 70 μm, about 50 μm and about 60 μm, between about 60 μm and about 125 μm, about 60 μm and about 115 μm, about 60 μm and about 100 μm, about 60 μm and about 90 μm, about 60 μm and about 80 μm, about 60 μm and about 70 μm, between about 70 μm and about 125 μm, about 70 μm and about 115 μm. about 70 μm and about 100 μm, about 70 μm and about 90 μm, about 70 μm and about 80 μm, between about 80 μm and about 125 μm, about 80 μm and about 115 μm, about 80 μm and about 100 μm, about 80 μm and about 90 μm, between about 90 μm and about 125 μm, about 90 μm and about 115 μm, about 90 μm and about 100 μm, between about 100 μm and about 125 μm, about 100 μm and about 115 μm, between about 115 μm and about 125 μm, about 20 μm, 30 μm, 40 μm, 50 μm, 60 μm, 70 μm, 80 μm, 90 μm, 100 μm, 115 μm, or about 120 μm. The nozzle is inert to both the solvent and the compressed fluid used in the methods.

The solvent comprise acetone, DCM, or combinations thereof. The solvent should comprise at least about 80%, 85%, or 90% by weight of the overall solution.

The compressed fluid is capable of forming a supercritical fluid under the conditions used, and the solute that forms the particles is poorly soluble or insoluble in the compressed fluid. As is known to those of skill in the art, a supercritical fluid is any substance at a temperature and pressure above its critical point, where distinct liquid and gas phases do not exist. Steps (a), (b), and (c) of the methods of the disclosure are carried out under supercritical temperature and pressure for the compressed fluid, such that the compressed fluid is present as a supercritical fluid during these processing steps.

The compressed fluid can serve as a solvent for and can be used to remove unwanted components in the particles. Any suitable compressed fluid may be used in the methods of the disclosure; exemplary such compressed fluids are disclosed in U.S, Patent Nos. 5833891 and 5874029. in one non-limiting embodiment, suitable supercritical fluid-forming compressed fluids and/or anti-solvents can comprise carbon dioxide, ethane, propane, butane, isobutane, nitrous oxide, xenon, sulfur hexafluoride and trifluoromethane. The anti-solvent recited in step (d) to cause further solvent depletion, is a compressed fluid as defined above, and may be the same compressed fluid used in steps (a-c), or may be different. In one embodiment, the anti-solvent used in step (d) is the same as the compressed fluid used in steps (a-c). In a preferred embodiment, the compressed fluid and the anti-solvent are both super-critical carbon dioxide.

In all cases, the compressed fluid and anti-solvent should be substantially miscible with the solvent while the compound to be precipitated should be substantially insoluble in the compressed fluid, i.e., the compound, at the selected solvent/compressed fluid contacting conditions, should be no more than about 5% by weight soluble in the compressed fluid or anti-solvent, and preferably is essentially completely insoluble.

The supercritical conditions used in the methods of the disclosure are typically in the range of from 1× to about 1.4×, or 1× to about 1.2× of the critical temperature of the supercritical fluid, and from 1× to about 7×, or 1× to about 2×, of the of the supercritical pressure for the compressed fluid.

It is well within the level of those of skill in the art to determine the critical temperature and pressure for a given compressed fluid or anti-solvent. In one embodiment, the compressed fluid and anti-solvent are both super critical carbon dioxide, and the critical temperature is at least 31.1° C. and up to about 60° C., and the critical pressure is at least 1071 psi and up to about 1800 psi. In another embodiment, the compressed fluid and anti-solvent are both super critical carbon dioxide, and the critical temperature is at least 35° C. and up to about. 55° C., and the critical pressure is at least 1070 psi and up to about 1500 psi. It will be understood by those of skill in the art that the specific critical temperature and pressure may be different at different steps during the processing.

Any suitable pressurizable chamber may be used, including but not limited to those disclosed in WO2016/197091 or in U.S. Pat. Nos. 5,833,891 and 5,874,029. Similarly, the steps of contacting the atomized droplets with the compressed fluid to cause depletion of the solvent from the droplets; and contacting the droplets with an anti-solvent to cause further depletion of the solvent from the droplets, to produce particles of the compound can be carried out under any suitable conditions, including but not limited to those disclosed in U.S. Pat. Nos. 5,833,891 and 5,874,029.

The flow rate can be adjusted as high as possible to optimize output but below the pressure limitations for the equipment, including the nozzle orifice. In one embodiment, the flow rate of the solution through the nozzle has a range from about 0.5 mL/min to about 30 mL/min. In various further embodiments, the flow rate is between about 0.5 mL/min to about 25 mL/min, 0.5 mL/min to about 20 ml/min, 0.5 mL/min to about 15 ml/min, 0.5 mL/min to about 10 mL/min, 0.5 mL/min to about 4 mL/min, about 1 mL/min to about 30 mL/min, about 1 mL/min to about 25 mL/min, about 1 mL/min to about 20 mL/min, 1 mL/min to about 15 mL/min, about 1 mL min to about 10 mL/min, about 2 Ml/min to about 30 mL/min, about 2 mL/min to about 25 mL/min, about 2 mL/min to about 20 mL/min, about 2 mL/min to about 15 mL/min, or about 2 mL/min to about 10 mL/min. The solution of drug subject to the flow rate can be any suitable concentration, such as between about 1 mg/ml and about 80 mg/ml.

In one embodiment, the methods further comprise receiving the plurality of particles through the outlet of the pressurizable chamber; and collecting the plurality of particles in a collection device, such as disclosed in WO2016/197091.

In another aspect, the disclosure provides compound particles prepared by the method of any embodiment or combination of embodiments of the disclosure.

EXAMPLES

Lapatinib free base (FB) was obtained from Accel Pharmtech or BOC Sciences. Material was stored protected from light in temperature and humidity monitored cabinet.

In one particular exemplary method, a solution of 12 mg/ml of lapatinib was prepared in acetone. The nozzle and a sonic probe were positioned in the pressurizable chamber approximately 9 mm apart, A stainless steel mesh filter with approximately 20 nm holes was attached to the pressurizable chamber to collect the precipitated lapatinib nanoparticles. The supercritical carbon dioxide was placed in the pressurizable chamber of the manufacturing equipment and brought to approximately 1200 psi at about 38 ° C. and a flow rate of 4 to 12 kg per hour. The sonic probe was adjusted to an amplitude of 60% of maximum output at a frequency of 20 kHz. The acetone solution containing the lapatinib was pumped through the nozzle at a flow rate of 2 mL/minute for approximately 25 minutes. The precipitated lapatinib particles were then collected from the supercritical carbon dioxide as the mixture was pumped through the stainless steel mesh filter. The filter containing the nanoparticles of lapatinib was opened and the resulting product was collected from the filter.

In another particular exemplary method, a solution of 6 mg/ml of lapatinib was dissolved in dichloromethane. The nozzle and a sonic probe were positioned in the pressurizable chamber approximately 9 mm apart. A sintered stainless steel mesh filter with approximately 20 nm holes was attached to the pressurizable chamber to collect the precipitated lapatinib particles. The supercritical carbon dioxide was placed in the pressurizable chamber of the manufacturing equipment and brought to approximately 1200 psi at about 37° C. and a flow rate of 4-12 kg per hour. The sonic probe was adjusted to an amplitude of 60% of maximum output at a frequency of 20 kHz. The dichloromethane solution containing the lapatinib was pumped through the nozzle at a flow rate of 2 mL/minute for approximately 50 minutes, The precipitated lapatinib particles were then collected from the supercritical carbon dioxide as the mixture was pumped through the stainless steel mesh filter. The filter containing the nanoparticles of lapatinib was opened and the resulting product was collected from the filter.

Feasibility Study

Lapatinib free base was evaluated for solubility in supercritical fluid carbon dioxide ($scCO_2$) and a variety of organic solvents. Three precipitation runs (approximately 600-700 mg) were conducted on the RC612B precipitation unit, according to examples provided above. Solvent was the single variable modified between each group of three precipitations. The precipitates were analyzed by laser diffraction to determine PSD, BET sorptometry to determine SSA, SEM to determine habit and support PSD and SSA data, and PXRD to determine crystalline/amorphous form.

PSD analyses were conducted on a Malvern Mastersizer™ 3000 using the Aero S™ dispersion unit according to manufacturer's instructions.

SSA determination analyses were conducted on a Porous Materials, Inc., Automated BET Sorptometer BET-202A according to manufacturer's instructions.

Figure 3:
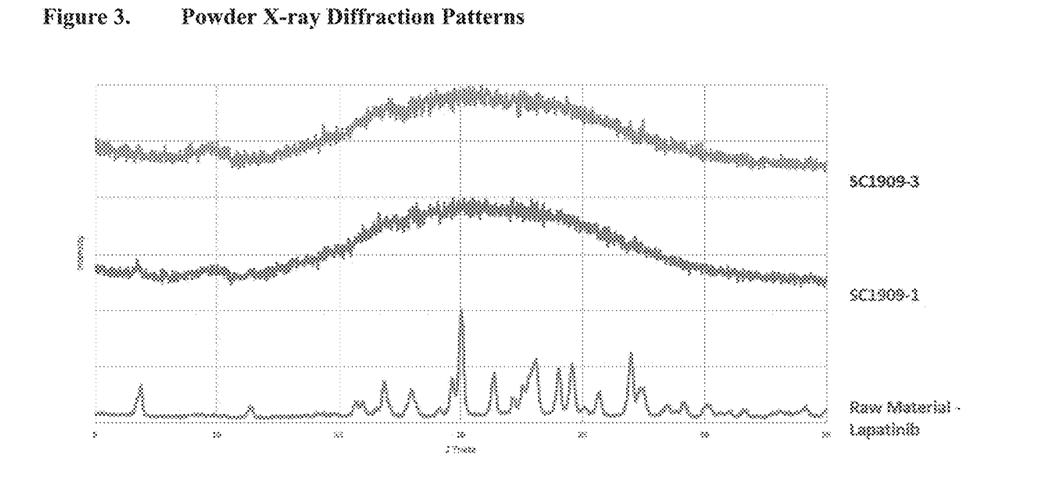
Figure 4:
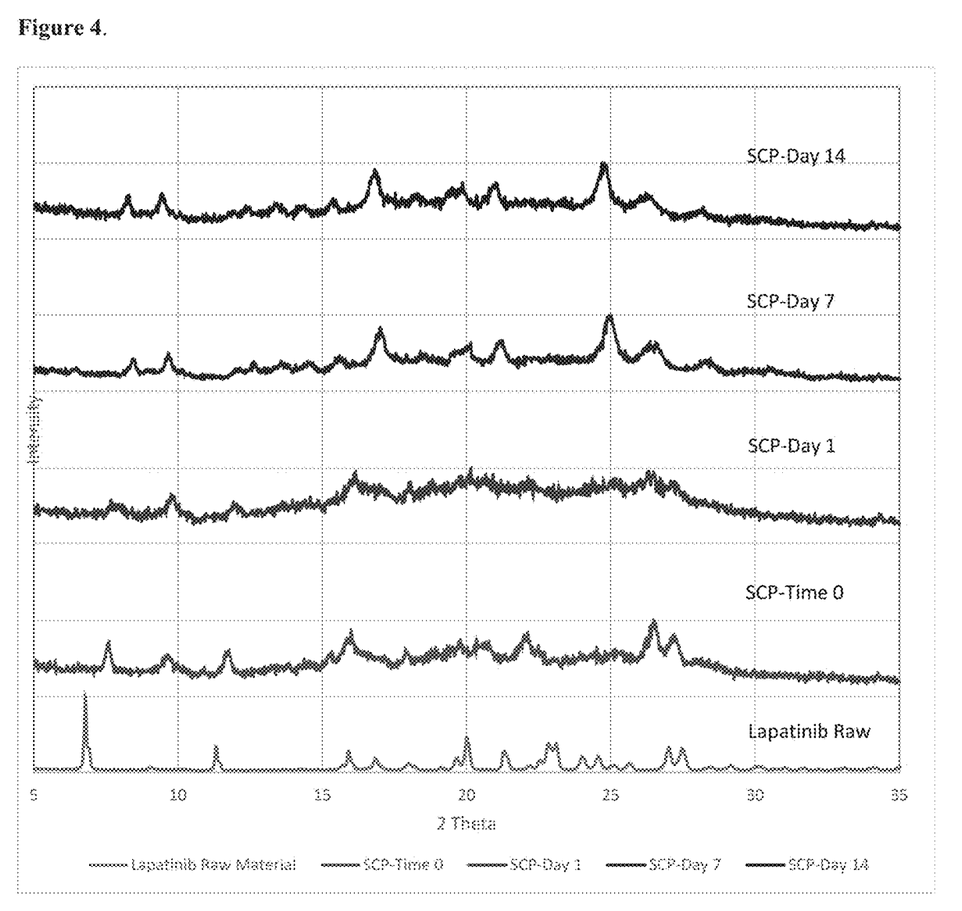

PXRD analyses were conducted on a Siemens D 5000 X-ray Diffractometer. PXRD scanned from 5 to 35 2θ degrees at a rate of 0.02 2θ degrees/second and 1 second per step according to manufacturer's instructions. Data is shown in FIGS. 3 and 4.

Figure 1:
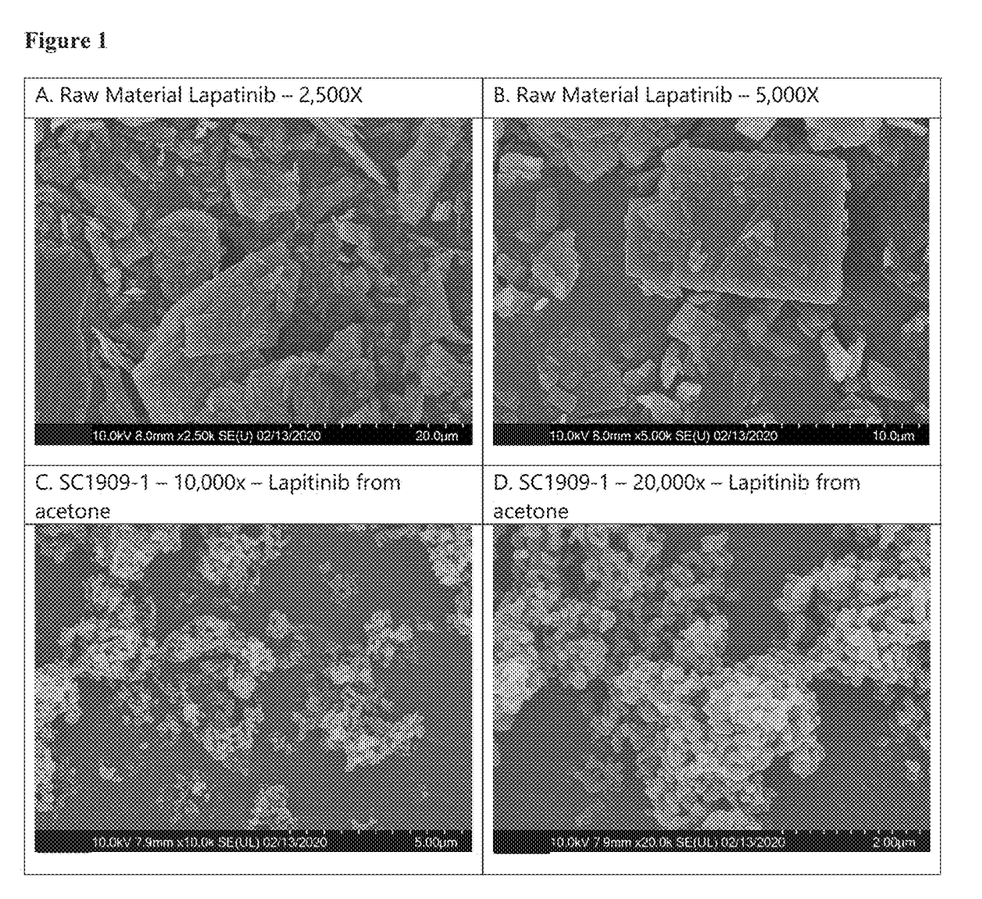
Figure 2:
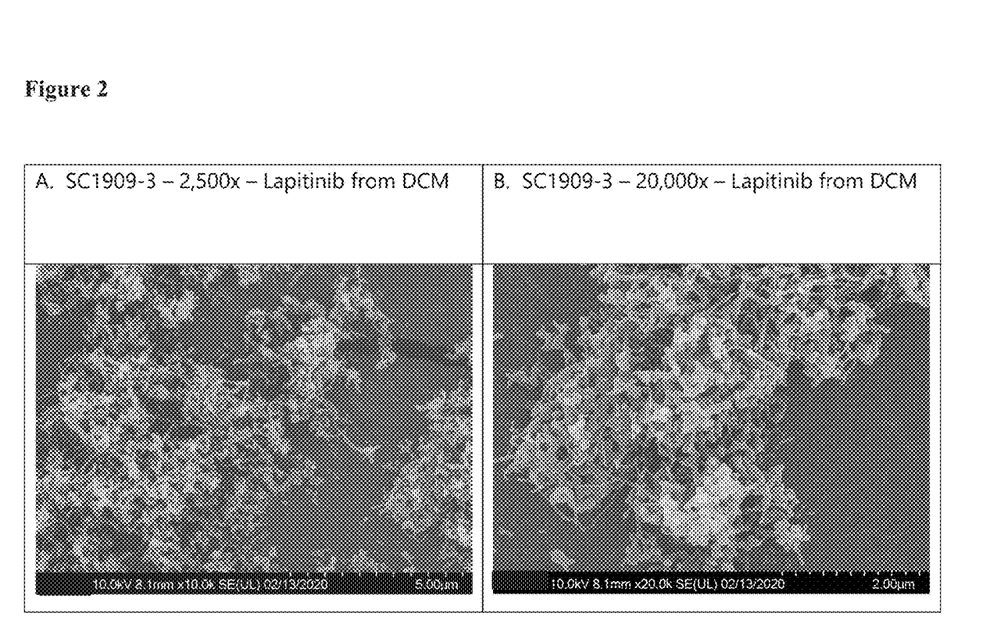

SEM was conducted on a Hitachi 8130 SEM, SEM micrographs can be found in FIGS. 1 and 2.

Lapatinib was precipitated from three solvents, acetone, hexafluoro isopropanol (HFIP), and dichloromethane (DCM). SC1909-1 and SC1909-3 (acetone and DCM) runs resulted in yields >78%; however, SC1909-2 (HFIP) run yielded ~31%. This low yield may be attributed to the high solubility of lapatinib in NIP, resulting in a binary solubility effect with the $scCO_2$, Following precipitation, the materials produced were analyzed using the techniques outlined in the analytical testing section.

After initial feasibility studies were conducted, lapatinib was precipitated from acetone at 9.9 mg/mL in a scale up, 7 gram run. Precipitated from the scaled-up run were analyzed by laser diffraction to determine PSD, SEM to support PSD data and determine habit, PXRD to determine crystalline/amorphous form, and bulk/tapped B/T density. These materials were also used for dissolution for comparison to unprocessed/raw material. In addition, samples were taken and placed on a short-term stability study (14 days) with open and closed containers for the three time points (excluding $T_0$): $T_{1d}$, $T_{7d}$, and $T_{14d}$. PXRD and appearance tests were conducted at each time point.

Two different powder patterns were observed during analysis by PXRD of lapatinib (FIG. 3). The first was of the raw material which was crystalline, and the second was of the processed materials from all solvents exhibiting the same amorphous phase. Amorphous powders very often are unstable and convert to crystalline forms. A 14 day stability study monitored by PSRD was conducted at room temperature which showed the conversion of the amorphous powder to a crystalline form after 7 days. Results are shown in FIG. 4. Because the conversion time was short and the subsequent characterization testing was conducted more than 7 days from when the particles were prepared, the dissolution testing was conducted on the crystalline form of the SCP lapatinib.

Particle size distribution results are shown in Table 1.

TABLE 1

| PSD: Volume (μm) | Lapatinib Raw | Lapatinib Acetone | Lapatinib Solvent DCM | Lapatinib scale up Acetone |
|---|---|---|---|---|
| Dv-10 | 0.839 | 0.445 | 0.597 | 1.38 |
| Dv-50 | 6.59 | 2.10 | 3.80 | 7.21 |
| Dv-90 | 335 | 9.13 | 25.5 | 24.1 |
| SSA $m^2/g$ | 2.33 | 19.67 | 20.01 | 42.67 |
| Bulk density (g/cm3) (untapped) | | | | 0.021 |
| Tapped Density(g/cm3) | | | | 0.027 |

The studies show that lapatinib particles produced using acetone and DCM as solvents possess significantly increased specific surface areas.

Solubility studies

Evaluating FDA Dissolution Methods

Dissolution methods were evaluated using the FDA approved methods for solid oral dosage forms of lapatinib, and did not show discrimination between materials having different specific surface areas. These methods were conducted in acidic media where the solubility of lapatinib is relatively high. Because of the higher solubility in acidic media, very little difference was observed comparing the raw material and SCP lapatinib (data not shown)

Since lapatinib may be administered via intertumoral delivery, development of a discriminating dissolution method at neutral pH was desired. Development of a discriminating dissolution method at neutral pH (6.8 to 7.4) was pursued, as relevant for potential intra-tumoral delivery of the drug. The addition of organic solvents was used to increase the solubility of the compounds at neutral pH. The solubility study was conducted at the following conditions:

Methanol/water ratios of 25/75, 50/50, and 75/25 (v/v)

Ethanol/water ratios of 25/75. 50/50, and 75/25 (v/v)

Solubility was determined by using a shake-flask method. The drug was added in excess to each solution prepared in duplicate. The vials were placed on a mechanical shaker for 24 hours at 20-25 ° C. After shaking, solution was removed and filtered through a 0.2 μm PTFE syringe filter and analyzed by UV/Visible spectrophotometry.

The results for the organic solvent modifier solubility for lapatinib are shown in Table 2. For both solvents, lapatinib showed concentration dependent solubility. The overall solubility was slightly higher with ethanol at a lower concentration.

TABLE 2

Solubility of Lapatinib at Various Organic Solvent Concentrations

| Water to Organic Solvent Ratio | Concentration of Lapatinib Found (μg/mL) | |
|---|---|---|
| | Methanol | Ethanol |
| 75/25 | ND | ND |
| 50/50 | 31.5 | 156 |
| 25/75 | 249 | 247 |

Figure 5:
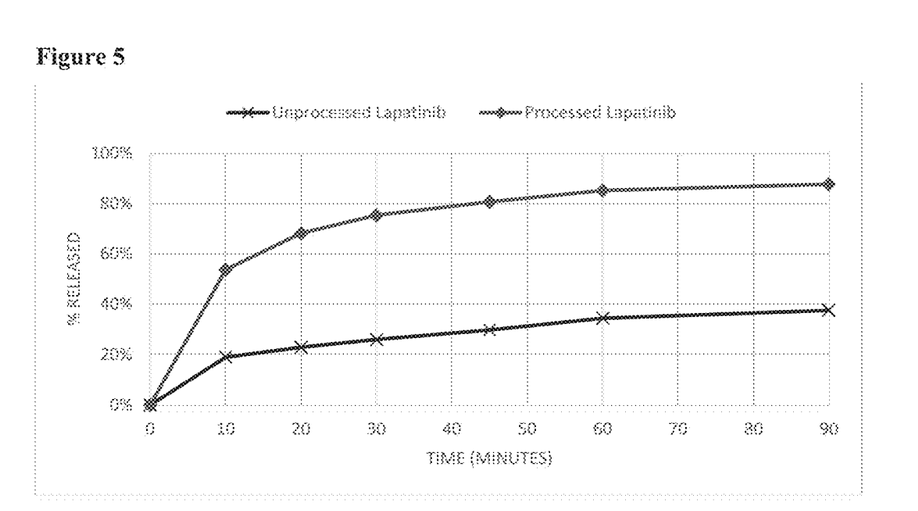

The media selected for dissolution testing was 500 mL of 50% ethanol-water with a paddle speed of 50 rpm, 37 C at pH=7. To meet sink conditions, 25 mg of drug was directly added to each vessel. Two vessels contained processed material with specific surface area measurement of 42.67 m$^2$/g and two vessels contained unprocessed material with specific surface area measurement of 1.60 m$^2$/g. Time points were taken at 5, 10, 20, 30, 45, 60, and 90 minutes. At each time point, a 5-mL aliquot was drawn and immediately filtered with a 0.45 μm PTFE syringe filter, discarding the first 1-mL of filtrate. The solution was then analyzed by UV/Visible spectrophotometry at a wavelength of 260 nm. Dissolution profiles are represented in FIG. 5 and show that lapatinib particles of the disclosure show greatly improved solubility compared to unprocessed lapatinib.

We claim:

1. A composition, comprising particles comprising at least 95% by weight of lapatinib, or a pharmaceutically acceptable salt thereof, wherein the particles have a specific surface area (SSA) of at least 11 m$^2$/g and have a mean particle size by volume distribution of between about 0.7 μm and about 8 μm.

2. The composition of claim 1, wherein the particles have a SSA of at least 15 m$^2$/g.

3. The composition of claim 1, wherein the particles have a SSA of at least 18 m$^2$/g.

4. The composition of claim 1, wherein the particles have a SSA of between 12 m$^2$/g and 50 m$^2$/g.

5. The composition of claim 1, wherein the particles have a mean particle size by volume distribution of between about 1 μm and about 8 μm.

6. The composition of claim 1, wherein the particles comprise at least 98% of lapatinib, or a pharmaceutically acceptable salt thereof.

7. The composition of claim 1, wherein the particles are uncoated and exclude polymer, protein, polyethoxylated castor oil and polyethylene glycol glycerides composed of mono-, di- and triglycerides and mono- and diesters of polyethylene glycol.

8. The composition of claim 1, wherein the composition comprises a suspension further comprising a pharmaceutically acceptable liquid carrier.

9. The composition of claim 1, further comprising one or more components selected from the group consisting of polysorbate, methylcellulose, polyvinylpyrrolidone, mannitol, and hydroxypropyl methylcellulose.

10. The composition of claim 1, wherein the particles have a mean bulk density less than about 0.100 g/cm$^3$, tapped or not tapped.

11. The composition of claim 1, wherein the pharmaceutically acceptable salt of lapatinib comprises lapatinib ditosylate monohydrate.

12. The composition of claim 2, wherein the particles have a mean bulk density between about 0.010 g/cm$^3$ and about 0.050 g/cm$^3$, tapped or not tapped.

13. The composition of claim 12, wherein the particles have a SSA of at least 18 m$^2$/g.

14. The composition of claim 12, wherein the particles have a SSA of between 15 m$^2$/g and about 50 m$^2$/g.

15. The composition of claim 14, wherein the lapatinib or pharmaceutically acceptable salt thereof comprises lapatinib ditosylate monohydrate.

16. The composition of claim 14, wherein the composition comprises a suspension further comprising a pharmaceutically acceptable liquid carrier.

17. The composition of claim 15, wherein the composition comprises a suspension further comprising a pharmaceutically acceptable liquid carrier.

* * * * *